(12) United States Patent
Hwang et al.

(10) Patent No.: US 11,969,150 B2
(45) Date of Patent: Apr. 30, 2024

(54) CLIP APPARATUS FOR ENDOSCOPE

(71) Applicant: FINE MEDIX CO., LTD., Daegu (KR)

(72) Inventors: Joong Bo Hwang, Daegu (KR); Seong Ho Hong, Daegu (KR)

(73) Assignee: FINE MEDIX CO., LTD., Daegu (KR)

( * ) Notice: Subject to any disclaimer, the term of this patent is extended or adjusted under 35 U.S.C. 154(b) by 795 days.

(21) Appl. No.: 16/647,757

(22) PCT Filed: Dec. 6, 2017

(86) PCT No.: PCT/KR2017/014185
§ 371 (c)(1),
(2) Date: Mar. 16, 2020

(87) PCT Pub. No.: WO2019/098446
PCT Pub. Date: May 23, 2019

(65) Prior Publication Data
US 2020/0275823 A1   Sep. 3, 2020

(30) Foreign Application Priority Data
Nov. 20, 2017   (KR) .................. 10-2017-0154635

(51) Int. Cl.
*A61B 1/00* (2006.01)
*A61B 1/005* (2006.01)
(Continued)

(52) U.S. Cl.
CPC ........ *A61B 1/0014* (2013.01); *A61B 1/00066* (2013.01); *A61B 1/0051* (2013.01);
(Continued)

(58) Field of Classification Search
CPC . A61B 1/0014; A61B 1/00066; A61B 1/0051; A61B 1/00137; A61B 1/00101;
(Continued)

(56) References Cited

U.S. PATENT DOCUMENTS 5,766,184 A * 6/1998 Matsuno ............... A61B 17/122
606/151
8,172,859 B2 * 5/2012 Matsuno ............ A61B 17/1285
606/151
(Continued)

FOREIGN PATENT DOCUMENTS

JP   2002-224124 A   8/2002
JP   2009-148442 A   7/2009
(Continued)

*Primary Examiner* — Brooke Labranche
(74) *Attorney, Agent, or Firm* — Bridgeway IP Law Group, PLLC; Jihun Kim

(57) ABSTRACT

The present disclosure relates to a clip apparatus for an endoscope, the clip apparatus having a simple driving part and enabling accurate and easy clip ligation and separation. The present disclosure provides a clip apparatus for an endoscope, the clip apparatus comprising: a handle part having a moving hole formed therein; a handle slider installed so as to be slidable in the handle part through the moving hole; an inner sheath rotatably connected to the inside of the handle part and extending to the outside of the handle part; a wire connected to the handle slider and disposed inside the inner sheath; an outer sheath disposed so as to cover the inner sheath; an outer handle coupled to the outer sheath so as to move the outer sheath along the length direction of the inner sheath; and a clip coupling part connected to one end of the wire and enabling the coupling of a clip.

13 Claims, 14 Drawing Sheets

(51) Int. Cl.
*A61B 17/12* (2006.01)
*A61B 17/122* (2006.01)
*A61B 17/128* (2006.01)
*A61B 17/00* (2006.01)

(52) U.S. Cl.
CPC ...... *A61B 17/12013* (2013.01); *A61B 17/122* (2013.01); *A61B 17/1285* (2013.01); *A61B 2017/00367* (2013.01); *A61B 2017/12004* (2013.01)

(58) Field of Classification Search
CPC ............ A61B 17/12013; A61B 17/122; A61B 17/1285; A61B 17/1227; A61B 2017/00367; A61B 2017/12004; A61B 2090/034; A61B 90/03
See application file for complete search history.

(56) References Cited

U.S. PATENT DOCUMENTS

| | | | |
|---|---|---|---|
| 8,419,751 B2 * | 4/2013 | Harada | A61B 17/1285 606/139 |
| 2006/0271066 A1 | 11/2006 | Kimura et al. | |
| 2013/0072945 A1 | 3/2013 | Terada | |
| 2014/0171974 A1 * | 6/2014 | Zhu | A61B 17/128 606/144 |

FOREIGN PATENT DOCUMENTS

| | | |
|---|---|---|
| JP | 2011-045535 A | 3/2011 |
| KR | 10-1554443 B1 | 9/2015 |
| KR | 10-2017-0041620 A | 4/2017 |
| WO | 96/14020 A1 | 5/1996 |

* cited by examiner

CLIP APPARATUS FOR ENDOSCOPE

TECHNICAL FIELD

The present disclosure relates to a clip apparatus for an endoscope, and more particularly, to a clip apparatus for an endoscope having a simple driving part and enabling accurate and easy clip ligation and separation.

BACKGROUND ART

A clip apparatus for an endoscope is an endoscope medical device used to ligate and suture biological tissues, and may be used to ligate through a clip or suture a perforated site in all situations related to the bleeding of body tissues such as arterial rupture due to an ulcer of stomach and colon. To this end, it is important to fix the clip to an accurate position.

Hereinafter, a conventional clip apparatus 1 for an endoscope will be described with reference to FIGS. 1 to 4.

As illustrated in FIG. 1, the conventional clip apparatus 1 for the endoscope is schematically composed of an outer sheath 10, an inner sheath 20 which is disposed inside the outer sheath 10, a wire 30 which is disposed inside the inner sheath 20, a connection hook 40, a base part 50, a slider part 60, and an outer support 70.

The slider part 60 includes a base outer cylinder 62 and a slider 64, the outer support 70 is slidably supported on the outside of the base outer cylinder 62, and one end of the wire 30 is connected and fixed to the slider 64.

One end of the outer sheath 10 is connected and fixed to the outer support 70 to be slid integrally, the base part 50 is provided with a fixed base 52 and a rotating base 54 which is rotatably supported thereby, and one end of the inner sheath 20 is connected and fixed to the center of the fixed base 52.

The rotating base 54 is a means which regulates the position of the slider part 60, and has a regulated position which regulates the slider part and an unregulated position which does not regulate the slider part. This will be described in detail below.

The connection hook 40 which is fixed to the front end of the wire 30 takes two states of an opened state and a closed state by cooperation with the inner sheath 20 so that the clip is coupled.

Next, a process of operating the conventional clip apparatus 1 for the endoscope will be described with reference to FIGS. 2 to 4.

The positions of the slider part 60 and the outer support 70 are determined by a plate spring and a positioning groove. A plate spring 65 is accommodated inside the slider 64, and the positioning thereof is performed as the plate spring 65 is elastically locked to any one of positioning grooves 53a, 53b, 53c which are formed in the base part 50. In addition, a plate spring 75 is also accommodated inside the outer support 70, and the positioning thereof is performed as the plate spring 75 is elastically locked to positioning groove 63a or 63b which is formed in the base outer cylinder 62.

First, as a preparing state for coupling the clip illustrated in FIG. 2, the plating spring 65 of the slider becomes locked to the positioning groove 53a, the plating spring 75 of the outer support becomes locked to the positioning groove 63a, and the connection hook 40 becomes opened by protruding from the inner sheath 20.

Next, as a step for coupling the clip illustrated in FIG. 3, first, the rotating base 54 is rotated clockwise with respect to the fixed base 52 to set it to a regulated position. At the regulated position, the outer shape of the rotating base 54 does not overlap with a part of the outer shape of the base 52 and a part thereof protrudes, such that when the slider part 60 is pushed into the base part 50 side, the slider part 60 is slidable with respect to the fixed base 52, but is not slidable with respect to the rotating base 54. Accordingly, when the clip is disposed on the connection hook 40 so as to be gripped and the slider part 60 is slid to the base part 50 side, the sliding of the slider part 60 is forcibly stopped in contact with the rotating base 54, the plate spring 65 of the slider is locked to the positioning groove 53b. As a result, the wire 30 connected to the slider and the connection hook 40 fixed to the front end of the wire are buried into the inner sheath 20, and the connection hook 40 is closed, thereby coupling the clip. At this time, the clip protrudes from the front end of the inner sheath 20.

Next, although not illustrated in the drawings, by sliding the outer support 70 to the clip side in order to insert the clip apparatus into the body so that the plate spring 75 of the outer support is locked to the positioning groove 63b, it is possible to integrally slide forward the outer sheath 10 which is connected to the outer support 70. Accordingly, from the inner sheath 20 to the clip may be buried inside the outer sheath 10, and after the clip enters the body, the outer support 70 is slid again to the slider part 60 side so that the plate spring 75 of the outer support is locked to the positioning groove 63a.

After entering the body as described above, the clip is disposed at a suitable position for ligating the clip. When the position of the clip is completely adjusted, the rotating base 54 is rotated counterclockwise with respect to the fixed base 52 to set it to the non-regulated position. At the non-regulated position, the outer shape of the rotating base 54 and the outer shape of the fixed base 52 overlap with each other to form the same shape, such that when the slider part 60 is pushed to the base part 50 side, the slider part 60 is slidable with respect to the rotating base 54 as well as the fixed base 52.

In addition, when the slider part 60 is slid to the base part 50 side, as illustrated in FIG. 4, the slider part 60 is slid to the rotating base 54 as well as the fixed base 52, such that the plate spring 65 of the slider is locked to the positioning groove 53c. As a result, the wire 30 which is connected to the slider is additionally drawn into the inner sheath 20 and the clip is also buried into the inner sheath 20. Accordingly, similarly to the closed state of the connection hook, the clip is also in the closed state, thereby ligating the clip.

Finally, when the ligation of the clip is completed, as illustrated in FIG. 2, the slider part 60 is slid to the distal end side of the base part 50, that is, in the opened state of the connection hook 40 and the operation is terminated by opening and separating the grip of the clip by the connection hook 40.

As may be seen in the above process, in order to couple, separate, or ligate the conventional clip, a method is used, in which the conventional clip apparatus is driven by sliding the slider part and the wire connected thereto or the outer support and the outer sheath connected thereto so that the plate spring is locked to the suitable positioning groove.

However, there are problems in that not only the configuration of the conventional clip apparatus is complicated because the conventional clip apparatus includes the plurality of plate springs and positioning grooves, but also the operation process thereof is very cumbersome because the conventional clip apparatus has the rotating base, in addition to the fixed base, to rotate them in the proper direction according to the operation process. In addition, there are problems in that, in order to separate the clip, the slider part is needed to be slid back to the distal end side of the base part, it is cumbersome to separate the clip because the clip is separated through the separate opening of the connection hook, and it is not possible to attempt to open and close the clip several times in order to ligate the clip to an accurate position because it is difficult to repeatedly open and close the clip.

DETAILED DESCRIPTION OF THE INVENTION

Technical Problem

The present disclosure is intended to solve the above problems, and an object of the present disclosure is to provide a clip apparatus for an endoscope having a simple driving part and enabling accurate and easy clip ligation and separation.

Technical Solution

An embodiment of the present disclosure for achieving the object provides a clip apparatus for an endoscope including a handle part which is formed with a moving hole, a handle slider which is installed to be slidable on the handle part through the moving hole, an inner sheath which is connected rotatably to the inside of the handle part and extend to the outside of the handle part, a wire which is connected to the handle slider and disposed inside the inner sheath, an outer sheath which is disposed to surround the inner sheath, an outer handle which is coupled to the outer sheath to move the outer sheath along the longitudinal direction of the inner sheath, and a clip coupling part which is connected to one end of the wire and configured to couple a clip.

In addition, the clip apparatus for the endoscope may further include a stopper which is provided detachably between the handle part and the outer handle.

The stopper may have a detachable part which may be spread and contracted to surround the outer sheath at both sides thereof.

The clip coupling part may include a connection part connected to one end of the wire and a bending part configured to detachably couple the clip.

The bending part may be composed of a pair of coupling arm parts which extend to face each other, and one coupling arm part may be bent to contact the other coupling arm part.

The connection part may include an insertion hole into which the wire may be inserted.

In addition, the clip apparatus for an endoscope may further include a clip which is coupled to the clip coupling part, and the clip may include a pair of clip arm parts which extend in a spreading configuration to be openable and closable, gripping parts which are formed to protrude from the ends of the pair of clip arm parts to the inside of the pair of clip arm parts and are placed opposite to each other to be engaged with each other, and a tightening ring which adjusts the opening and closing of the pair of clip arm parts.

The pair of clip arm parts may be each formed with a protrusion part, and as the tightening ring is press-fitted into the protrusion part, the clip may be gripped.

The tightening ring may adjust the opening and closing of the clip while moving on the pair of clip arm parts and until the tightening ring is press-fitted into the protrusion part.

The inner width of the tightening ring at a location where the pair of clip arm parts is disposed may be formed to be greater than the width of a portion where the tightening ring moves on the pair of clip arm parts, and may be formed to be equal to or smaller than the width of the protrusion part.

The pair of clip arm parts may be formed of an elastic body to have a spreading property.

An outer diameter (L1) of the tightening ring may be formed to be greater than an inner diameter (L2) of the inner sheath.

When the handle slider is slid to the handle part side, the tightening ring may be press-fitted into the protrusion part by being pushed and moved to the protrusion part side by the inner sheath.

When the tightening ring is press-fitted into the protrusion part and then the handle slider is slid to the handle part side, the bending part may be unfolded and the clip may be separated.

A space part where the outer sheath may be disposed may be formed between the handle part and the inner sheath.

In addition, the clip apparatus for the endoscope may further include a spring which is disposed within the moving hole to surround the wire.

When the spring is not compressed, the clip coupling part may be positioned inside the inner sheath.

A handle ring may be formed at one end of the handle part, and a handle part may be formed on the outer surface of the handle slider along the circumferential direction.

The sliding movement of the handle slider may be limited within a length of the moving hole of the handle part.

In addition, the present disclosure provides a clip including a pair of clip arm parts which extends in the form spread to be openable and closable, gripping parts which are formed to protrude from the ends of the pair of clip arm parts to the insides opposite to each other to be engaged with each other, a protrusion part which is formed on each of the pair of clip arm parts, and a tightening ring which adjusts the opening and closing of the pair of clip arm parts, and the gripping parts may be engaged with each other to be gripped as the tightening ring is press-fitted into the protrusion part.

Advantageous Effects

According to the clip apparatus of the present disclosure, by driving, with one handle slider, the wire connected thereto, the clip may be ligated and separated, such that the structure of the driving part is simple and the operation thereof is easy.

In addition, since the wire may also be rotated based on the rotation of the handle part, the clip which is connected to the wire may be rotated, thereby easily determining the direction of the clip, and other structures are not affected by the rotation.

In addition, since the opening and closing of the clip may be repeatedly performed until the clip is completed ligated, that is, until the tightening ring is press-fitted into the protrusion part, the opening and closing of the clip may be attempted several times to ligate the clip to the accurate position.

In addition, the clip apparatus of the present disclosure enters the target point inside the body and then removes the stopper so that the outer handle and the outer sheath connected thereto are pushed back to prevent the clip from being opened when the clip apparatus enters the body, thereby making the clip apparatus easily and safely enter the body.

In addition, the clip coupling part is not exposed to the outside of the inner sheath because the spring is included, thereby preventing the clip from being separated by the side load when the clip apparatus enters, and the spring is compressed to push the handle slider after the clip apparatus enters, thereby correcting the opening angle of the clip to be wider.

The effects of the present disclosure are not limited to the above-described effects, but should be understood to include all the effects inferable from the configurations of the disclosure described in the detailed description or claims of the present disclosure.

BEST MODE

Figure 1:
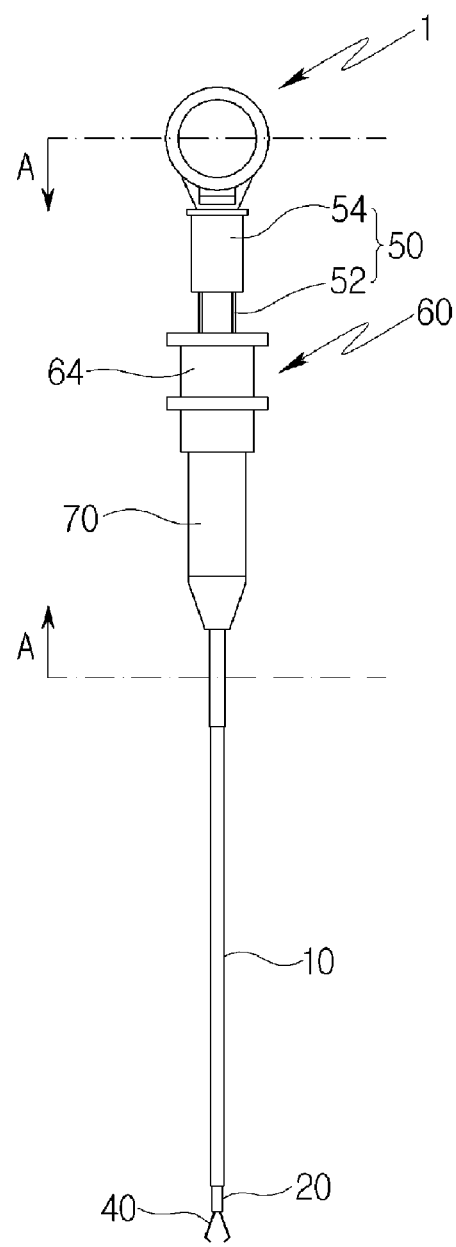
FIG. 1 is a front diagram illustrating a conventional clip apparatus for an endoscope.
Figure 2:
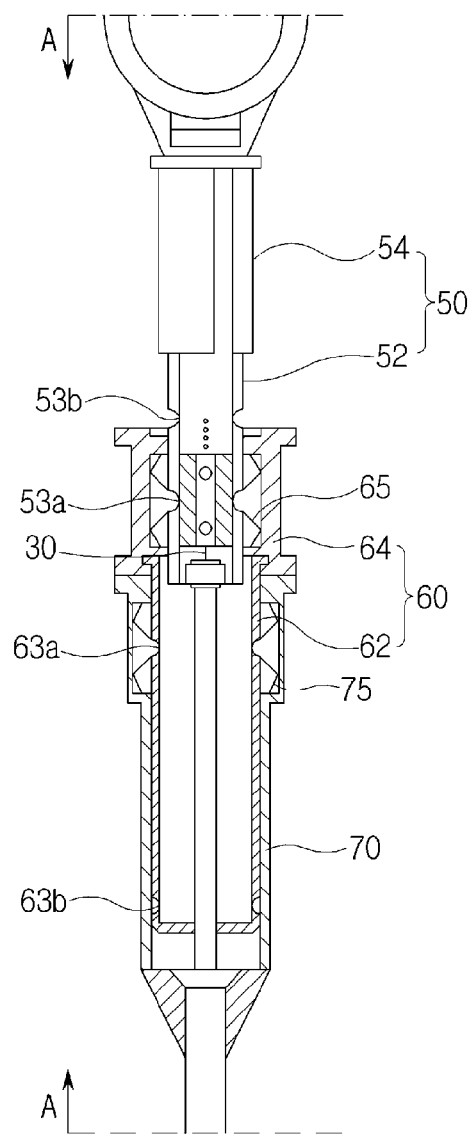
FIG. 2 is an enlarged cross-sectional diagram of a portion A of FIG. 1.
Figure 3:
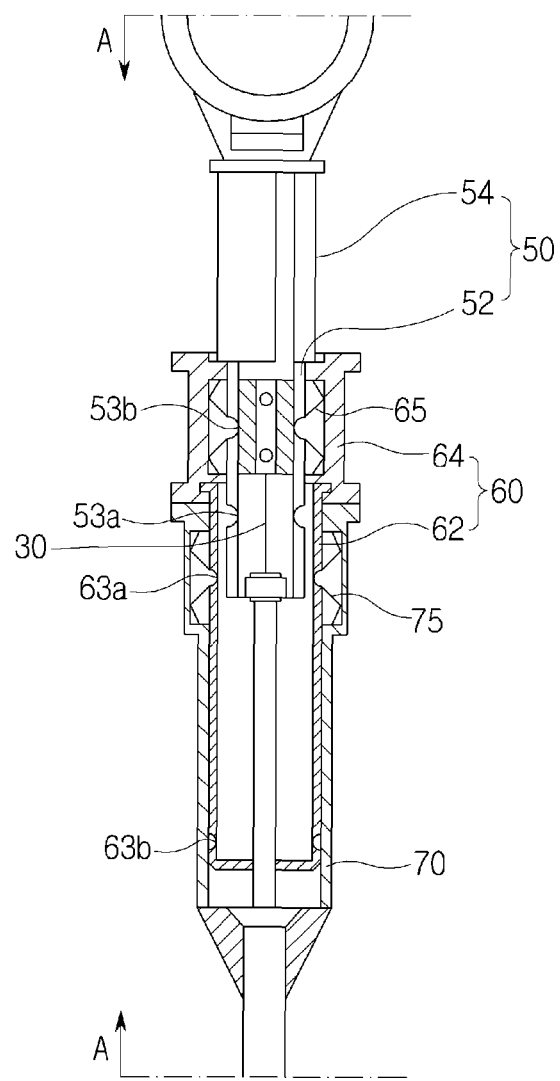
FIG. 3 is a cross-sectional diagram illustrating another state of FIG. 2.
Figure 4:
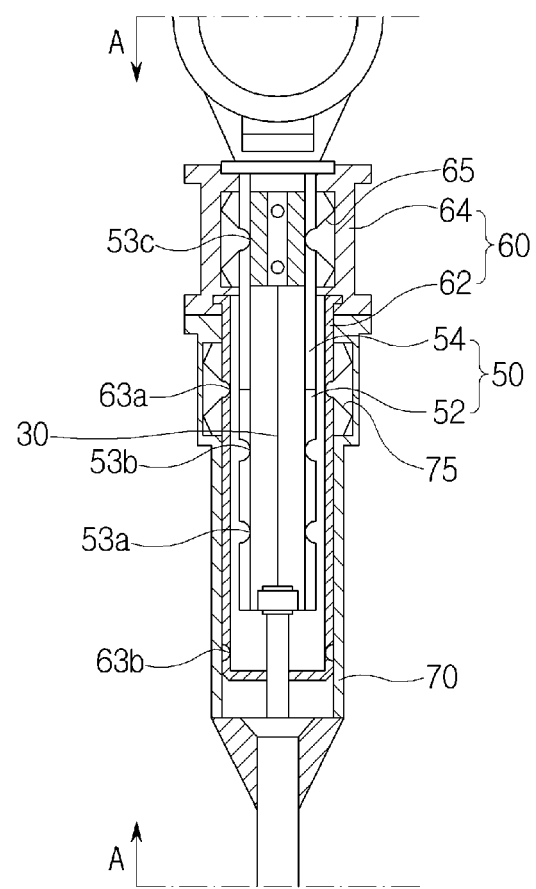
FIG. 4 is a cross-sectional diagram illustrating still another state of FIG. 2.

Hereinafter, a preferred embodiment of a clip apparatus for an endoscope according to the present disclosure will be described with reference to FIGS. 5 to 15.

In addition, terms to be described later are terms defined in consideration of functions in the present disclosure, which may vary according to intentions or customs of users or operators, and the following embodiments do not limit the scope of the present disclosure but are merely illustrative of the components recited in the claims of the present disclosure.

In order to clearly describe the present disclosure, parts irrelevant to the description are omitted, and the same or like components are denoted by the same reference numerals throughout the specification. Throughout the specification, when a part is said to "include" a component, it means that it may further include other components rather than excluding the other components unless otherwise stated.

Figure 5:
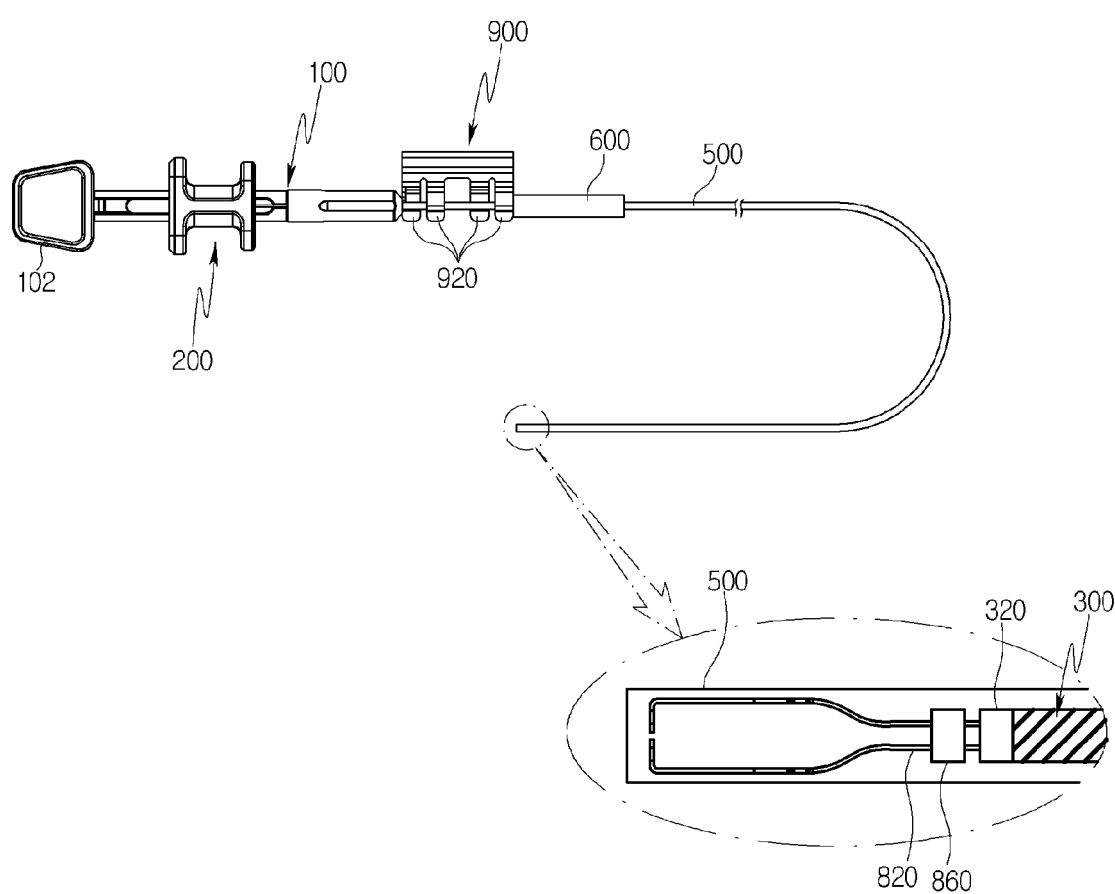
FIG. 5 is a front diagram illustrating a clip apparatus for an endoscope according to an embodiment of the present disclosure.
Figure 6:
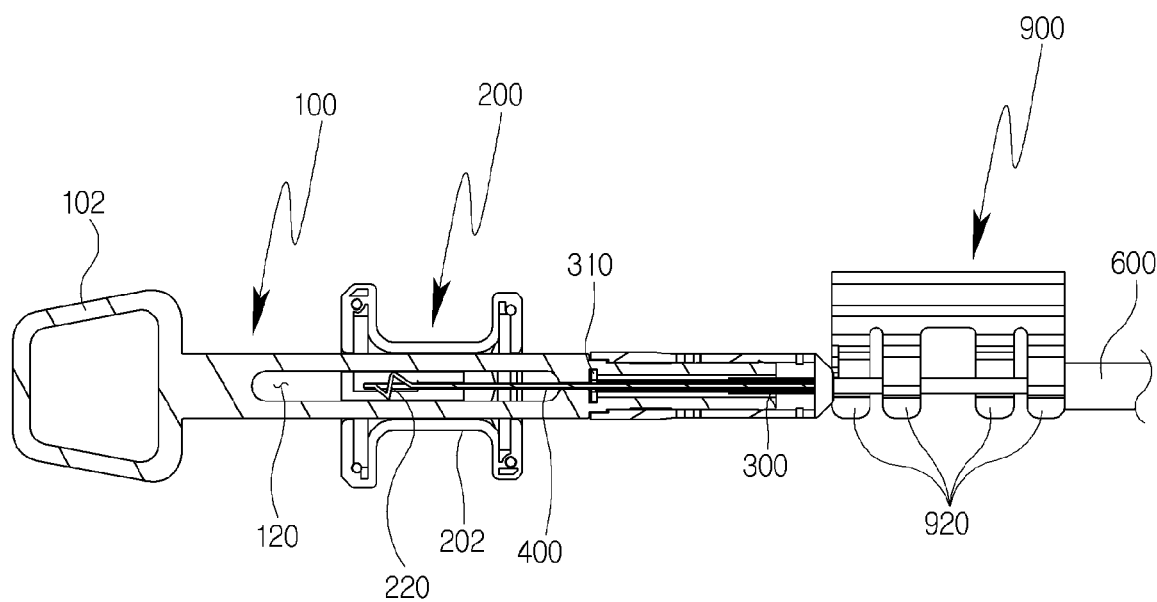
FIG. 6 is a partial cross-sectional diagram of FIG. 5.
Figure 7:
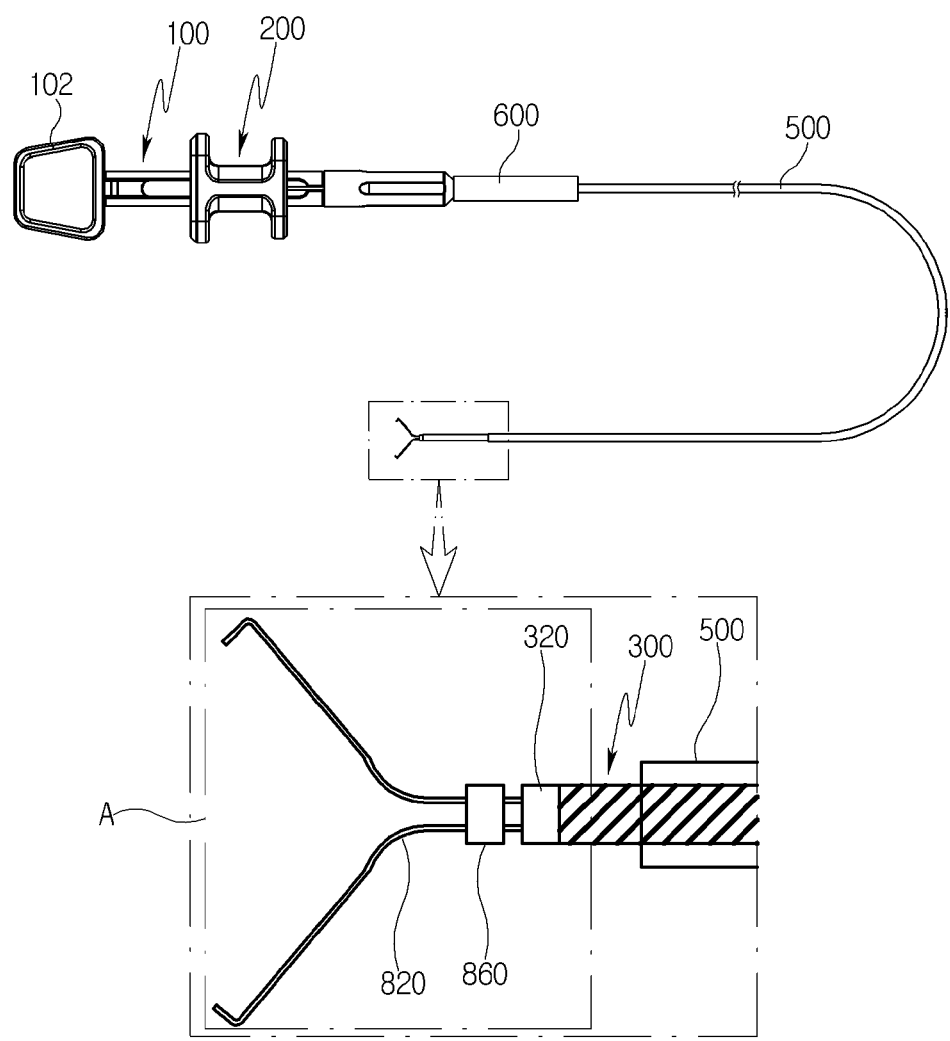
FIG. 7 is a front diagram illustrating a state of the clip apparatus for an endoscope illustrated in FIG. 5.
Figure 8:
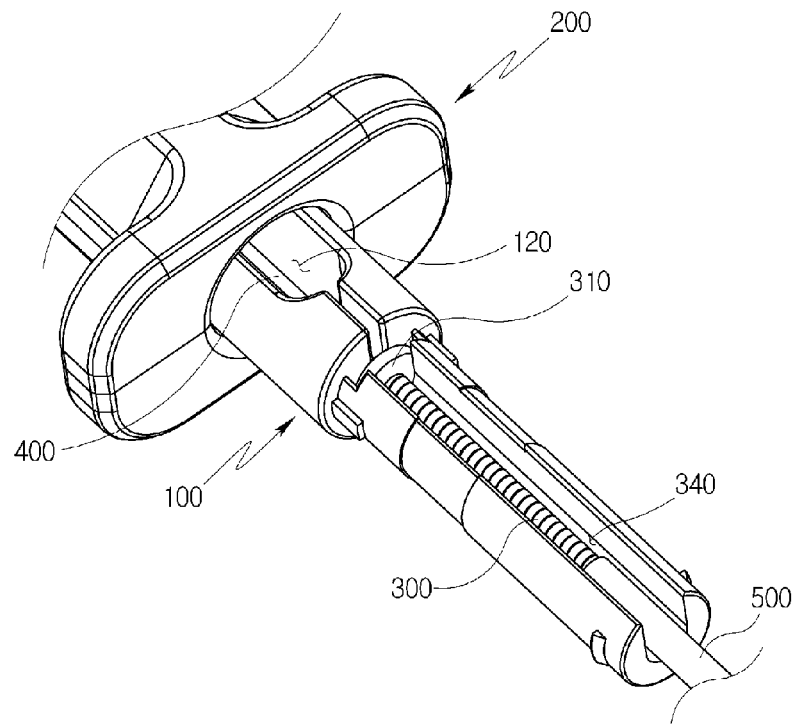
FIG. 8 is a perspective diagram in which a part of FIG. 5 is separated.
Figure 9:
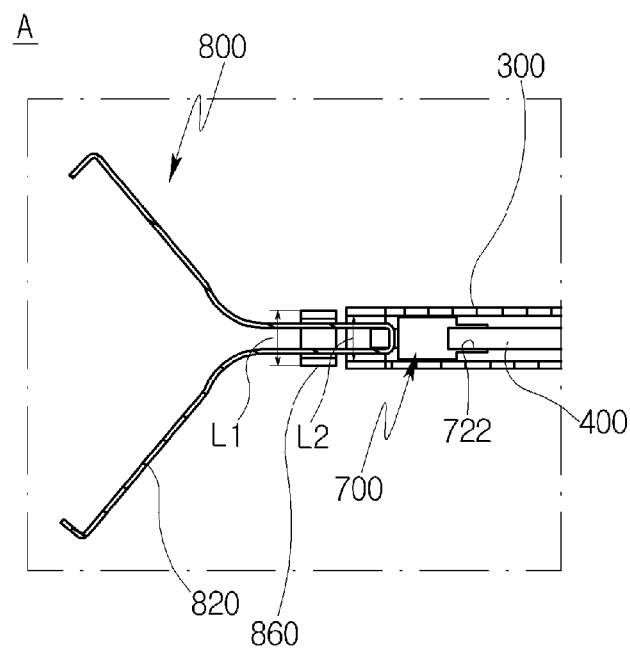
FIG. 9 is a cross-sectional diagram of a portion A of FIG. 7.
Figure 10:
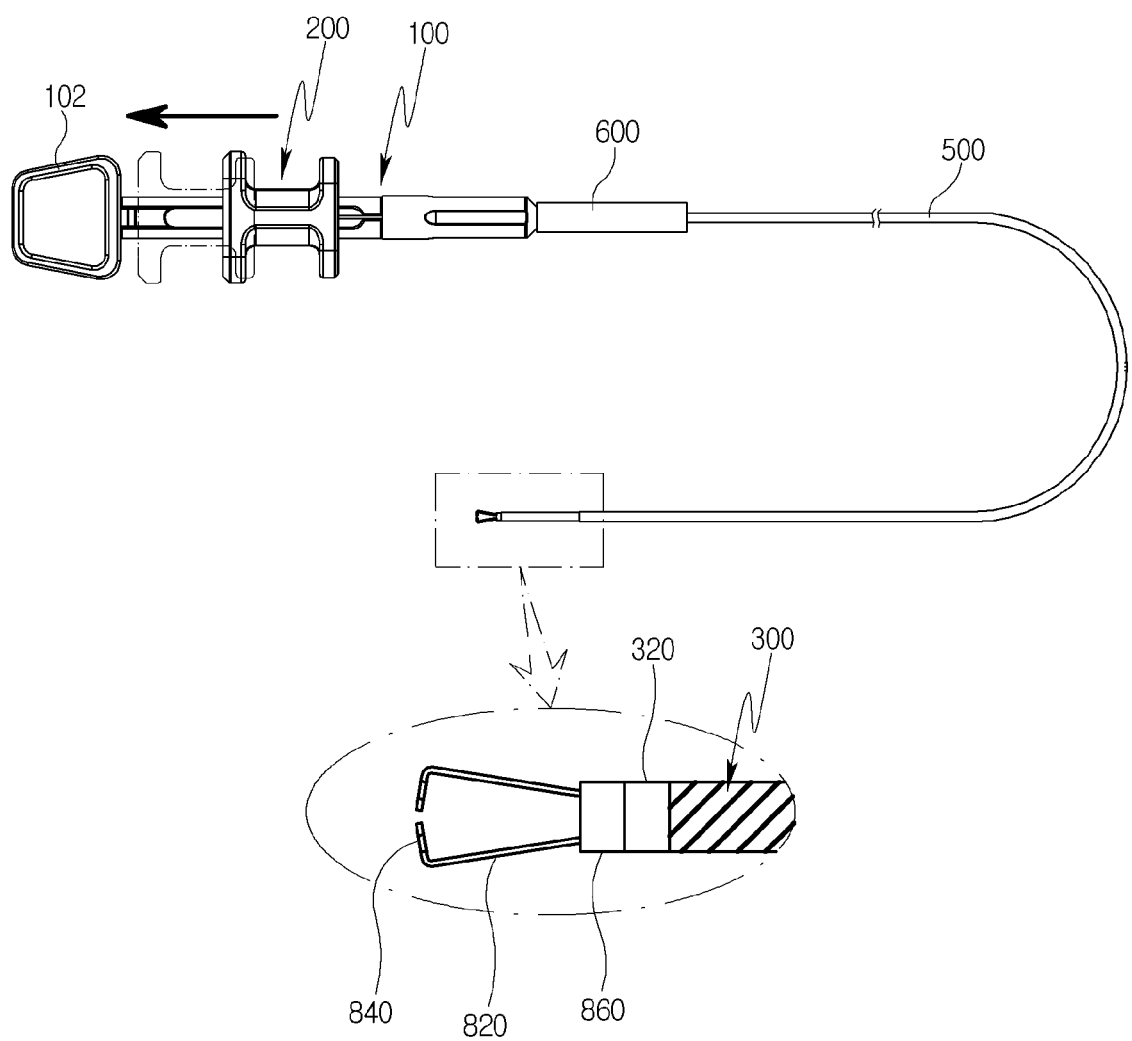
FIG. 10 is a front diagram illustrating a state of the clip apparatus for an endoscope illustrated in FIG. 5.
Figure 11:
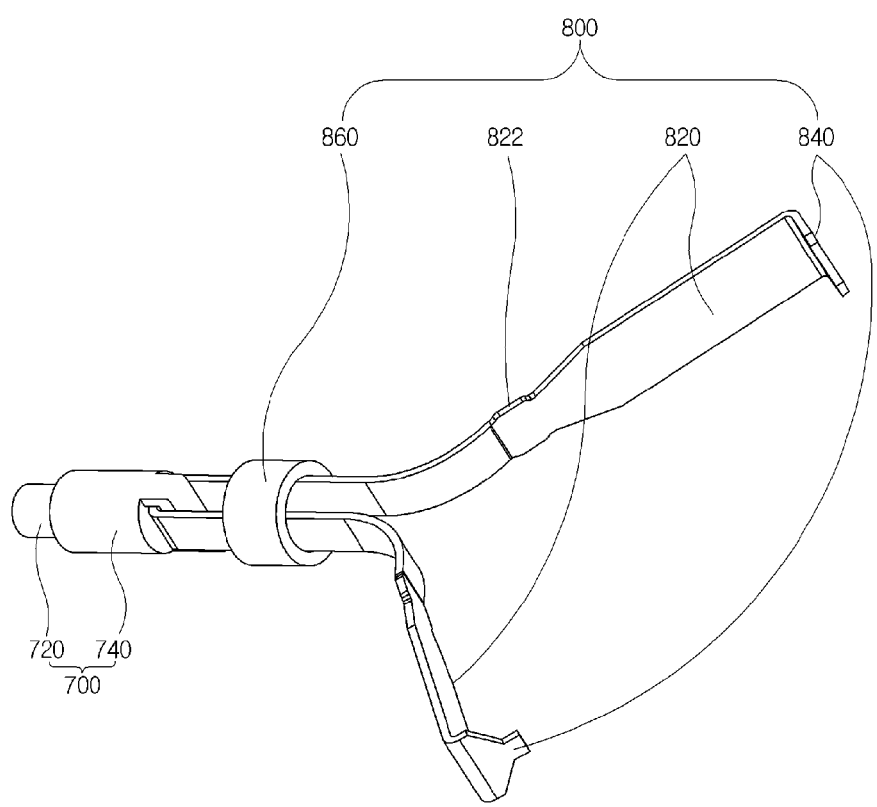
FIG. 11 is a perspective diagram separately illustrating a clip coupling part and a clip in FIG. 9.
Figure 12:
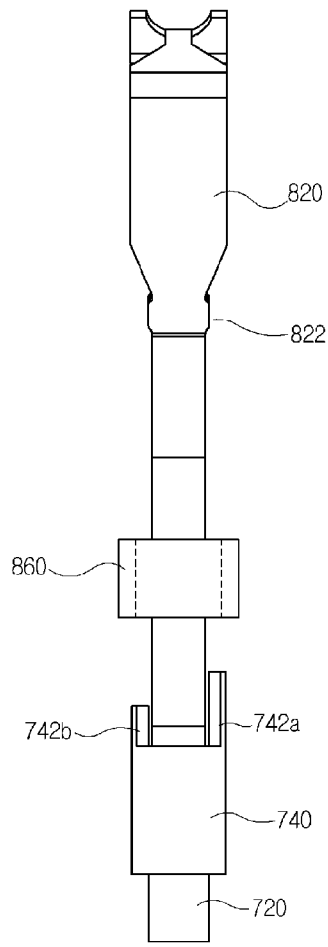
FIGS. 12 and 13 are side diagrams illustrating before and after coupling the clip coupling part and the clip of FIG. 11.
Figure 13:
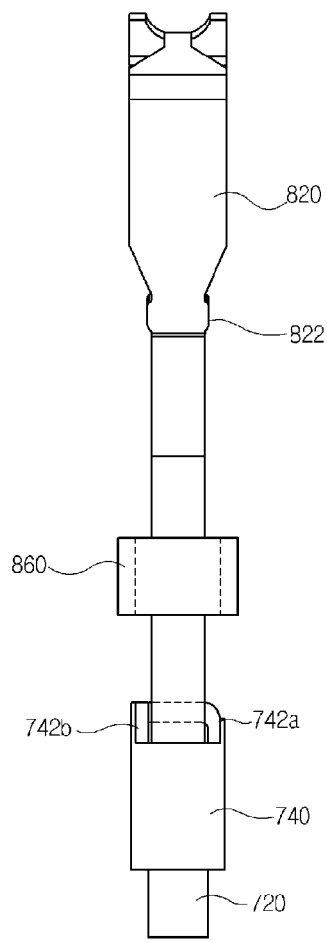
Figure 14:
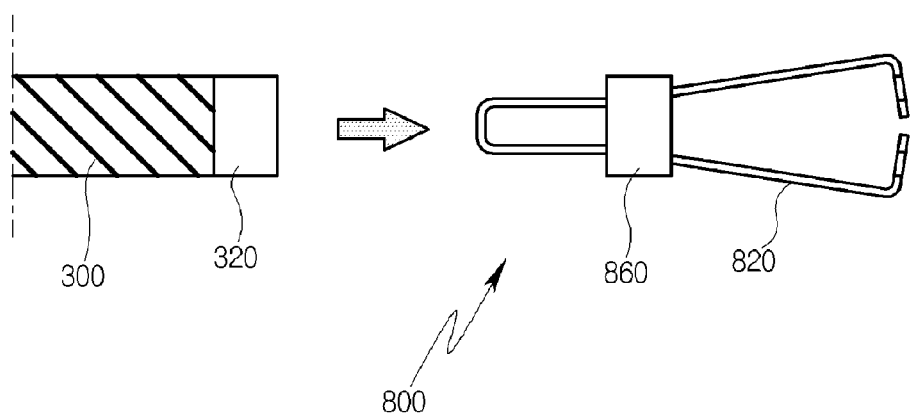
FIG. 14 is a diagram illustrating a state where the clip is separated in FIG. 10.
Figure 15:
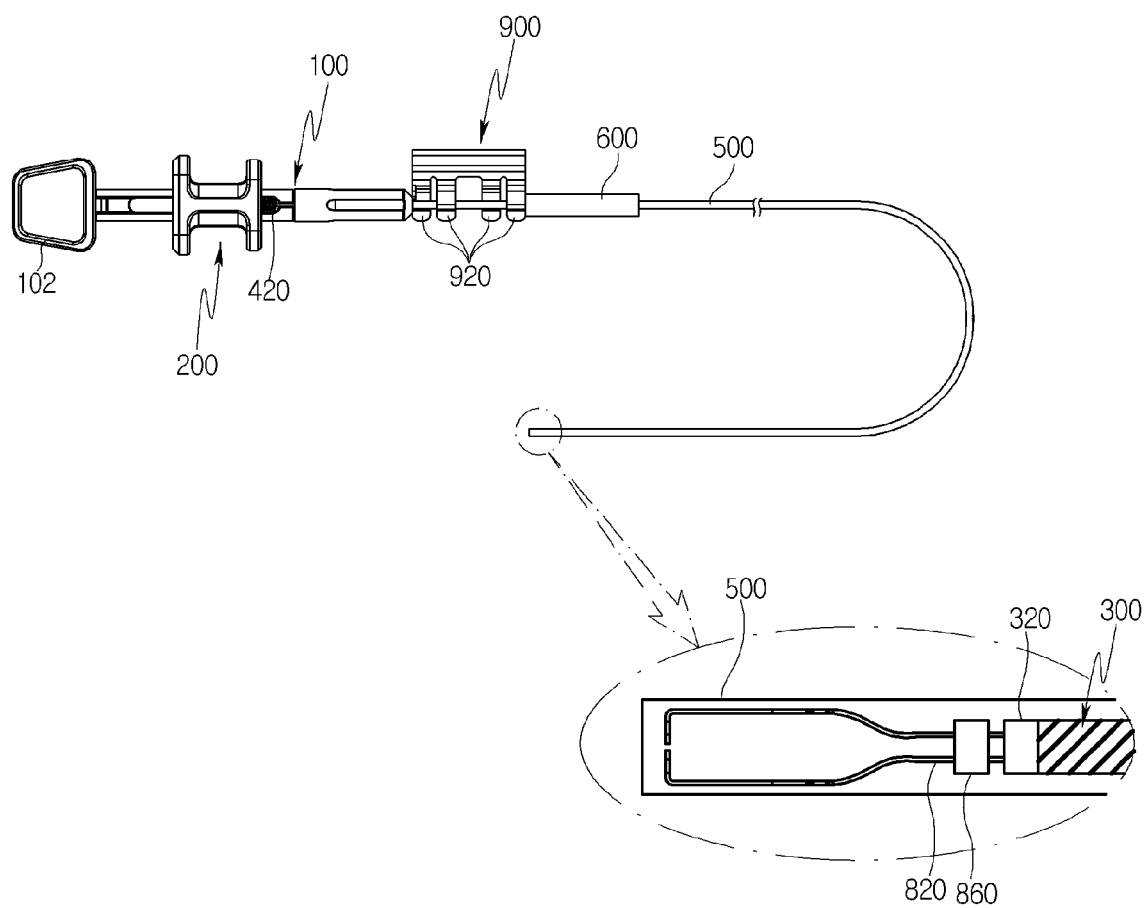
FIG. 15 is a front diagram illustrating a clip apparatus for an endoscope according to another embodiment of the present disclosure.

FIG. 5 is a front diagram illustrating a clip apparatus for an endoscope according to an embodiment of the present, FIG. 6 is a partial cross-sectional diagram of FIG. 5, FIG. 7 is a front diagram illustrating a state of the clip apparatus for an endoscope illustrated in FIG. 5, FIG. 8 is a perspective diagram in which a part of FIG. 5 is separated, FIG. 9 is a cross-sectional diagram of a portion A of FIG. 7, FIG. 10 is a front diagram illustrating a state of the clip apparatus for an endoscope illustrated in FIG. 5, FIG. 11 is a perspective diagram separately illustrating a clip coupling part and a clip in FIG. 9, FIGS. 12 and 13 are side diagrams illustrating before and after coupling the clip coupling part and the clip of FIG. 11, FIG. 14 is a diagram illustrating a state where the clip is separated in FIG. 10, and FIG. 15 is a front diagram illustrating a clip apparatus for an endoscope according to another embodiment of the present disclosure.

First, a structure of the clip apparatus for an endoscope according to an embodiment of the present disclosure will be described with reference to FIGS. 5 to 10.

The clip apparatus for an endoscope according to an embodiment of the present disclosure may be configured to largely include a clip part, a sheath part which may operate the clip part by the relative movement, a driving part which is connected to the sheath part to drive the movement of the sheath part.

Specifically, in the present embodiment, the driving part may be configured to include a handle part 100, a handle slider 200, and an outer handle 600, and the sheath part may be configured to include an inner sheath 300, a wire 400, and an outer sheath 500, and the clip part may include a clip coupling part 700 and a clip 800 which is detachably coupled to the clip coupling part 700.

The handle part 100 forms the body of the clip apparatus and is formed of an elongated cylindrical rod in the present embodiment.

A part of the handle part 100 may be formed with a moving hole 120 along the longitudinal direction, and the handle slider 200 to be described later may be provided to be slidable on the handle part 100 through the moving hole 120.

A handle ring 102 may be formed at one end of the handle part 100. Accordingly, a user may easily fix the clip apparatus according to the present disclosure by inserting his/her finger into the handle ring 102.

At this time, a friction groove may also be formed on the partial outer surface of the handle part 100 to prevent the handle slider 200 from being moved relatively with respect to the handle part 100 by a weak force.

The handle slider 200 is installed to be slidable on the handle part 100 through the moving hole 120. Specifically, the handle slider 200 may be fitted to penetrate the moving hole 120 and may be formed of a cylindrical column like the handle part 100.

The handle slider 200 may be formed in two separable structures to be fitted to penetrate both sides of the moving hole 120 of the handle part, and may be assembled when the clip apparatus is assembled.

A handle part 202 may be formed on the outer surface of the handle slider 200 in the circumferential direction. In the present embodiment, the handle part 202 may be formed of a groove which is formed on the outer circumferential surface of the handle slider 200 in the circumferential direction, thereby easily gripping the handle part 202 by hand. That is, the thumb may be fitted into the handle ring 102 and the handle part 202 may be gripped with the index finger and the middle finger, thereby easily moving the handle slider 200 back and forth with respect to the handle part 100.

Hereinafter, by defining, based on FIG. 5, the left, that is, the side where the handle part 100 is formed as the rear and the right, that is, the side where the clip 800 is coupled as the front, pushing the handle slider 200 into the clip 800 side will be described as forward movement, and the pulling the handle slider 200 to the handle ring 102 side will be described as backward movement.

At this time, the inside of the handle slider 200 may be formed with a coupling groove 220 configured to couple the wire 400 to be described later, and in the present embodiment, the coupling groove 220 is formed in a combination of a Z shape and a straight shape. The coupling structure of the wire 400 will be described in detail below.

In addition, the handle slider 200 is slidable within the moving hole 120 of the handle part, and the sliding movement thereof may be limited within the length of the moving hole 120.

That is, the handle slider 200 may move as forward as possible as illustrated in FIG. 5, and move as backward as possible as illustrated in FIG. 10. This will be described in detail in the operation process of the clip apparatus according to the present disclosure.

The inner sheath 300 is rotatably connected to the inside of the handle part 100 and is formed to extend to the outside of the handle part 100.

Specifically, as illustrated in FIG. 8, the inner sheath 300 is connected to the inside of the handle part 100 and the sliding movement is not possible forward or backward, but is connected to have a gap with the inner surface of the handle part 100 through an inner sheath ring 310 and is relatively rotatable with respect to the handle part 100.

The inner sheath 300 may be formed in a hollow long tubular shape having flexibility, and is formed of a coil tube in the present embodiment. In addition, an inner pipe tip 320 made of a rigid material may also be formed at the end of the inner sheath 300. Accordingly, as will be described in detail later, the inner pipe tip 320 may easily push a tightening ring 860 of the clip 800.

The outer sheath 500 is disposed to surround the inner sheath 300, and the outer sheath 500 is slidable along the longitudinal direction from the outside of the inner sheath 300. The outer sheath 500 may be formed in a hollow long tube shape having flexibility.

Specifically, a space part 340 in which the outer sheath 500 may be disposed may be formed between the handle part 100 and the inner sheath 300. Accordingly, one end portion of the outer sheath 500 may be moved within the space part 340. At this time, the end of the outer sheath 500 is preferably formed to be movable within the range of the space part 340.

To this end, the end of the outer sheath 500 may be formed with a locking part which is locked to the inside of the handle part 100 to prevent the outer sheath 500 from being separated to the outside.

In addition, the outer sheath 500 may be coupled to the outer handle 600 configured to move the outer sheath 500 along the longitudinal direction of the inner sheath 300.

In the present embodiment, the outer handle 600 is formed of a cylindrical rod which is coupled to surround a part of the outer sheath 500, and as described in detail below, may be coupled to a position which is spaced a certain length apart from the end of the outer sheath 500 in order to form a portion where a stopper 900 is detached, that is, to form one end portion of the outer sheath 500 for movement in the space part 340.

Specifically, the outer handle 600 is preferably coupled to be spaced apart from the end of the outer sheath 500 by a length at which the outer sheath 500 may be disposed within the space part 340. That is, as illustrated in FIG. 7, when the outer handle 600 contacts the handle part 100, one end portion of the outer sheath 500 may be disposed within the space part 340.

As described above, as the outer sheath 500 moves forward or backward through the outer handle 600, the clip 800 may be disposed within the outer sheath 500 or exposed to the outside of the outer sheath 500, thereby facilitating the entry of the clip apparatus. This will be described in detail in the operation process of the clip apparatus according to the present disclosure.

In addition, an outer pipe tip made of a rigid material may also be formed at the end of the outer sheath 500. Accordingly, the outer pipe tip may help the clip apparatus to easily enter upon entry.

The wire 400 is connected to the handle slider 200 and disposed inside the inner sheath 300.

Accordingly, the wire 400 may move forward and backward integrally with the handle slider 200, and the wire 400 is also rotated integrally as the handle part 100 and the handle slider 200 rotate.

As described above, the wire 400 may also rotate together based on the rotation of the handle part 100, and accordingly, the direction of the clip may be easily determined by the rotation of the clip 800 which is connected to the wire 400, and other structures are not affected by the rotation.

The wire 400 is composed of a wire having flexibility, is disposed to penetrate the inside of the inner sheath 300, and is slidable inside the inner sheath 300. To this end, the wire 400 is preferably formed longer in length than the inner sheath 300.

In the present embodiment, the wire 400 is coupled to the coupling groove 220 of the handle slider 200, as illustrated in FIG. 6, and formed to extend to the outside of the handle part 100 with being disposed inside the inner sheath 300 by penetrating the handle part 100. Specifically, the wire 400 may be fixed by being locked to the Z-shaped portion of the coupling groove 220.

In addition, since the wire 400 has a flexible property, a sus pipe may be further provided to surround the wire 400 to reinforce the straightness thereof. Specifically, the sus pipe may be formed to surround one end portion of the rear side of the wire 400, that is, one end portion of the portion of the wire 400 which is coupled to the coupling groove 220 of the handle slider, and formed to have a length of about 8 to 12 cm.

In addition, the clip apparatus may further include the stopper 900 which is detachably provided between the handle part 100 and the outer handle 600.

The stopper 900 is provided between the handle part 100 and the outer handle 600 so that the outer handle 600 and the outer sheath 500 connected thereto are not moved backward, when the clip apparatus according to the present disclosure enters a target point inside the body through an endoscope. Accordingly, when the clip apparatus enters the body, the outer handle 600 and the outer sheath 500 connected thereto are pushed back so that the clip 800 which is disposed inside the outer sheath 500 is not exposed to the outside, thereby enabling safer and easier entry.

The stopper 900 may be removed after the clip apparatus according to the present disclosure enters the target point inside the body. This will be described in detail in the operation process of the clip apparatus according to the present disclosure.

The stopper 900 is formed to have a detachable part which may be spread and contracted to surround the outer sheath 500 at both sides thereof, and in the present embodiment, the stopper 900 is formed of a structure in which four detachable parts 920, which surround one side of the outer sheath 500 alternately at both sides of the outer sheath 500, are connected to one, as illustrated in FIG. 5.

Next, the clip coupling part 700 configured to couple the clip 800 is connected to one end of the wire 400.

The clip coupling part 700 may include a connection part 720 which is connected to one end of the wire 400 and a bending part 740 configured to detachably couple the clip 800.

The bending part 740 is composed of a pair of coupling arm parts 742 extending to face each other, and one coupling arm part 742a may be bent to contact the other coupling arm part 742b. That is, as illustrated in FIGS. 12 and 13, the bending part 740 is composed of the pair of coupling arm parts 742 extending to face each other, and in the present embodiment, the one coupling arm part 742a is formed longer in length than the other coupling arm part 742b.

Accordingly, the one coupling arm part 742a may be bent toward the inside facing the other coupling arm part 742b to couple one end portion of the clip 800 as illustrated in FIG. 13, and the one coupling arm part 742a may have a flexible property to be bendable, and at the same time, have a constant strength, thereby keeping the clip 800 coupled.

As described above, the clip 800 may be coupled as the one coupling arm part 742a is bent to contact the other coupling arm part 742b, and at this time, the other coupling arm part 742b may be made of a rigid material.

In addition, as illustrated in FIG. 9, the connection part 720 may include an insertion hole 722 into which the wire 400 may be inserted. Accordingly, the wire 400 may be fixed by the welding with being inserted into the insertion hole 722.

As described above, when the clip 800 is coupled by the bending of the bending part 740 and then a tensile force is applied to the bending part 740, that is, when, as described later, a force of pulling the wire 400, connected to the handle slider 200, backward is applied to the bending part 740 by moving the handle slider 200 backward in a state where the clip 800 is ligated to the lesion site, the bending part 740 is unfolded in the original state and the coupled state of the clip 800 is released as illustrated in FIG. 12, such that as illustrated in FIG. 14, the clip 800 may be separated from the clip coupling part 700. This will be described in detail in the operation process of the clip apparatus according to the present disclosure.

Next, describing the clip 800 in detail with reference to FIGS. 9 and 11, the clip 800 is connected to one end portion of the wire 400 through the clip coupling part 700. Specifically, the clip 800 may include a pair of clip arm parts 820 which extends in the form which is spread to be openable and closable, gripping parts 840 which are formed to protrudes from the ends of the pair of clip arm parts 820 to the insides opposite to each other to be engaged with each other, and the tightening ring 860 which adjusts the opening and closing of the pair of clip arm parts 820.

A protrusion part 822 is formed on each of the pair of clip arm parts 820, and the clip 800 may be gripped as the tightening ring 860 is forcibly press-fitted into the protrusion part 822.

The pair of clip arm parts 820 is formed side by side in a substantially U shape and then extend while being spread to both sides thereof to be openable and closable, and are generally formed of a metal plate having elasticity. As described above, the pair of clip arm parts 820 may be formed of an elastic body and may have a spreading property when no external physical force is applied thereto.

At this time, each of the arm parts 820 may also be formed with a hole to allow tissues to escape when the tissues are excessively picked up. By forming the hole as described above, even when the tissues are excessively picked up, it is possible to prevent the case where the clip is not ligated well or the clip is spread again.

The protrusion part 822 is formed on each of the pair of clip arm parts 820, and in the present embodiment, the protrusion parts 822 are formed side by side in a U shape at each of the clip arm parts 820, and then partially spread to both sides thereof.

The tightening ring 860 is disposed to be movable forward and backward on the pair of clip arm parts 820 until being press-fitted into the protrusion part 822, and may be made of metal. Accordingly, until the tightening ring 860 is press-fitted into the protrusion part 822, the tightening ring 860 may adjust the opening and closing of the clip 800 while moving on the pair of clip arm parts 820, and the opening and closing of the clip 800 may be repeatedly performed, thereby attempting to the opening and closing of the clip 800 several times in order to ligate the clip 800 to the accurate position.

When the tightening ring 860 is located at the rear with respect to the pair of clip arm parts 820, the pair of clip arm parts 820 are opened, and when the tightening ring 860 is located at the front with respect to the pair of clip arm parts 820, the pair of clip arm parts 820 are closed.

At this time, referring to FIG. 11, the inner width at the position where the pair of clip arm parts 820 are disposed in the tightening ring 860 is preferably formed to be greater than the width of a portion where the tightening ring 860 moves in the pair of clip arm parts 820, and equal to or smaller than the width of the protrusion part 822.

That is, the inner width at each position where the pair of clip arm parts 820 are disposed side by side inside the tightening ring 860 may be formed greater than the U-shaped portion where the tightening ring 860 moves in the pair of clip arm parts 820, thereby easily performing the forward and backward movements of the tightening ring 860, and may be formed to be equal to or smaller than the width of the protrusion part 822 to be forcibly press-fitted, thereby enabling the ligation of the clip 800.

The clip arm part 820 from the protrusion part 822 to the gripping part 840 may be formed to have the width greater than the protrusion part 822 to prevent the tightening ring 860 press-fitted into the protrusion part 822 from being separated forward.

In addition, as illustrated in FIG. 9, an outer diameter (L1) of the tightening ring 860 is formed greater than an inner diameter (L2) of the inner sheath 300. Accordingly, when the handle slider 200 is moved backward and the wire 400 connected thereto is pulled backward, the tightening ring 860 does not enter the inner sheath 300 but is pushed by the inner sheath 300, thereby moving forward from the clip 800.

The gripping parts 840 are formed to protrude from the ends of the pair of clip arm parts 820 to the insides opposite to each other to be engaged with each other, and are engaged with each other until the pair of clip arm parts 820 are closed. At this time, it is preferable that one gripping part is formed with a portion of protruding in a certain shape, and the other gripping part is formed with a portion which includes a groove having a certain shape corresponding thereto, so that the gripping parts are engaged with each other.

Next, a clip apparatus for an endoscope according to another embodiment of the present disclosure will be described with reference to FIG. 15.

The clip apparatus for an endoscope according to another embodiment of the present disclosure has the same structure as the clip apparatus for an endoscope described above, but further includes a spring 420 which is disposed within the moving hole 120 to surround the wire 400.

The present embodiment is particularly applicable to the case where the clip apparatus according to the present disclosure is used in the procedure through a windingly twisted path rather than straight, such as the oral cavity and anus of the body.

As described above, since the sheath part of the clip apparatus according to the present disclosure is also twisted when the procedure is performed along the windingly complicated path and the wire 400 is wound around the inside of the inner sheath 300 in a wider radius than when the procedure is performed through a straight section, the wire 400 may be pulled backward and the clip 800 coupled thereto may also be pulled backward, thereby reducing the opening angle.

In order to compensate for this, the wire 400 may be applied longer in preparation for the case where the sheath part according to the present disclosure is looped. That is, in the aforementioned embodiment, as illustrated in FIG. 5, when the handle slider 200 is disposed at the maximum forward position, the clip coupling part 700 is formed to be positioned inside the inner sheath 300, but in the present embodiment, when the handle slider 200 is disposed at the maximum forward position, the clip coupling part 700 may be formed to be exposed to the outside of the inner sheath 300.

At this time, although the wire 400 is formed lengthily, the spring 420 may be further included as in the present embodiment in order to prevent the clip coupling part 700 from being exposed to the outside of the inner sheath 300.

That is, the spring 420 maintains the handle slider 200 not to be disposed at the maximum forward position when no force is applied thereto, and as a result, the clip coupling part 700 is positioned inside the inner sheath 300 when the spring 420 is not compressed.

Thereafter, when the clip 800 approaches the lesion site for the procedure, the narrowed opening angle of the clip 800 may be corrected by pushing the handle slider 200 to the maximum forward position while compressing the spring 420.

Accordingly, even when the wire 400 is formed lengthily in preparation for the procedure through the winding path, the clip coupling part 700 may be prevented from being exposed to the outside of the inner sheath 300, thereby preventing the clip 800 from being separated by the side load when the clip apparatus enters, and after the clip apparatus enters, the opening angle of the clip may be corrected to be widened by compressing the spring 420 and pushing the handle slider 200.

Next, a process will be described, in which the clip apparatus for an endoscope according to an embodiment of the present disclosure is operated to stop the bleeding of or suture the biological tissues.

First, the state for entering the clip apparatus for an endoscope according to the present disclosure into the body will be described with reference to FIGS. 5 and 6.

This is a state where both the handle slider 200 and the outer handle 600 are moved to the maximum forward position. Accordingly, the wire 400 which is connected to the handle slider 200 is also positioned as forward as possible, and at this time, the clip coupling part 700 is disposed inside the inner sheath 300 and the pair of clip arm parts 820 of the clip are opened.

In addition, the outer sheath 500 which is connected to the outer handle 600 is also positioned as forward as possible to all surround from the inner sheath 300 to the clip 800. At this time, the clip 800 is in the opened state but becomes spread because the clip 800 is not ligated by the outer sheath 500. As will be described later, when the outer sheath 500 is moved backward again, the clip 800 returns to the opened state.

In addition, since the stopper 900 is provided between the handle part 100 and the outer handle 600, the outer handle 600 and the outer sheath 500 connected thereto are not pushed backward, and accordingly, the clip 800 is not exposed to the outside, and accordingly, the clip apparatus according to the present disclosure may more safely and easily enter the body.

Next, a state where the clip 800 is exposed to the outside of the outer sheath 500 after the clip apparatus enters the body will be described with reference to FIG. 7.

When the clip apparatus completely enters the body as described above, the position of the clip 800 is needed to be properly adjusted to ligate the clip 800 to the lesion site inside the body. To this end, the clip 800 is needed to be exposed to the outside of the outer sheath 500, and the outer sheath 500 is needed to be moved backward.

To this end, the stopper 900 may be removed and the outer handle 600 and the outer sheath 500 connected thereto may be pulled and moved backward, and accordingly, the clip 800 is opened while coming out to the outside of the outer sheath 500.

Accordingly, in such a state, the pair of clip arm parts 820 are positioned at a target position, and the direction of the clip 800 which is connected through the wire 400 may also be properly adjusted by rotating the handle part 100.

That is, by gripping the outer handle 600 and integrally rotating the handle part 100 and the handle slider 200, the wire 400, the clip coupling part 700, and the clip 800 which are connected to the handle slider 200 may be rotated.

Next, the state where the clip 800 is ligated will be described with reference to FIG. 10.

As described above, when the position of the clip 800 is completely adjusted, the clip 800 may be ligated by pulling the handle slider 200 backward.

Specifically, when the handle slider 200 is pulled backward, the wire 400 and the clip coupling part 700 which are connected thereto are also pulled backward. At this time, since the outer diameter of the tightening ring 860 of the clip is greater than the inner diameter of the inner sheath 300 and the tightening ring 860 may not enter the inner sheath 300, only the pair of clip arm parts 820 which are coupled by the bending part 740 of the clip coupling part 700 are pulled backward, and accordingly, the tightening ring 860 moves forward on the pair of clip arm parts 820, thereby making the clip 800 closed.

Until the tightening ring 860 is forcibly press-fitted into the protrusion part 822 of the pair of clip arm parts 820, the tightening ring 860 may adjust the opening and closing of the clip 800 while moving the handle slider 200 forward or backward.

In order to ligate the clip 800, when an operator feels the feeling which is locked to the handle slider 200, that is, when the operator feels that the tightening ring 860 is locked to the protrusion part 822, the tightening ring 860 is forcibly press-fitted into the protrusion part 822 by applying a force to and pulling the handle slider 200, and the clip 800 is ligated.

Lastly, as illustrated in FIG. 10, when the clip 800 is ligated and then the handle slider 200 is pulled as backward as possible by applying a force thereto, the clip 800 is ligated and fixed to the lesion site, such that only the wire 400 and the clip coupling part 700 are moved backward and a tensile force is generated in the bending part 740 of the clip coupling part.

Accordingly, the one coupling arm part 742a which has been bent to couple the clip 800 is unfolded and the clip 800 may be separated as illustrated in FIG. 14. Finally, the clip apparatus for an endoscope escapes to the outside with the clip 800 positioned as it is.

According to the clip apparatus for an endoscope according to the present disclosure, by driving, with one handle slider, the wire connected thereto, the clip may be ligated and separated, such that not only the structure of the driving part is simple but also the operation thereof is easy.

The present disclosure is not limited to the aforementioned specific embodiments and descriptions, and various modifications may be made by those skilled in the art without departing from the subject matter of the present disclosure as claimed in the claims, and such modifications fall within the protection scope of the present disclosure.

INDUSTRIAL APPLICABILITY

The present disclosure relates to a clip apparatus for an endoscope, and more particularly, to a clip apparatus for an endoscope having a simple driving part, and enabling the accurate and easy clip ligation and separation.

What is claimed is:

1. A clip apparatus for an endoscope, comprising:
a handle body having a moving hole formed therein;
a handle slider slidably coupled to the handle body through the moving hole;
an inner sheath rotatably disposed inside the handle body and extending to an outside of the handle body;
a wire connected to the handle slider and disposed inside the inner sheath;
an outer sheath disposed to surround the inner sheath;
an outer handle coupled to the outer sheath to move the outer sheath along a longitudinal direction of the inner sheath; and
a clip coupler connected to one end of the wire,
wherein the clip coupler comprises:
a cylindrical body having a distal end surface and a proximal end surface, the distal end surface being closed;
a connection protrusion protruded from the proximal end surface of the cylindrical body and connected to the one end of the wire; and
a pair of coupling arms extending from the distal end surface of the cylindrical body and facing each other,
wherein one of the pair of coupling arms has a length greater than that of the other of the pair of coupling arms such that the one coupling arm is bent to contact the other coupling arm which is not bent,
wherein the one coupling arm has a greater flexibility than that of the other coupling arm, further comprising a clip which is configured to be coupled to the clip coupler, wherein the clip comprises:
a pair of clip arms extending in a spreading configuration to be opened or closed;
gripping tips protruding from ends of the pair of clip arms and placed opposite to each other to be engaged with each other; and
a tightening ring configured to adjust opening and closing of the pair of clip arms,
wherein each of the pair of clip arms has protrusion portions formed on side surfaces thereof, and when the tightening ring is press-fitted into the protrusion portions, the clip is configured to be gripped,
wherein the clip apparatus is configured such that when the handle slider is slid toward the handle body, the tightening ring is press-fitted into the protrusion portions by being pushed and moved toward the protrusion portions by the inner sheath, and the one coupling arm is unfolded so as for the clip to be separated from the clip coupler.

2. The clip apparatus of claim 1, further comprising a stopper detachably disposed between the handle body and the outer handle.

3. The clip apparatus of claim 2,
wherein the stopper has detachable fingers which are spreadable and contractible to surround the outer sheath at both sides thereof.

4. The clip apparatus of claim 1,
wherein the connection protrusion comprises an insertion hole into which the wire is insertable.

5. The clip apparatus of claim 1,
wherein the tightening ring is configured to adjust opening and closing of the clip while moving on the pair of clip arms until the tightening ring is press-fitted into the protrusion portions.

6. The clip apparatus of claim 5,
wherein an inner width of the tightening ring at a location where the pair of clip arms are disposed is greater than a width of a portion where the tightening ring moves on the pair of clip arms, and is equal to or smaller than a width of the respective protrusion portion.

7. The clip apparatus of claim 1,
wherein the pair of clip arms are formed of an elastic body having a spreading property.

8. The clip apparatus of claim 1,
wherein an outer diameter (L1) of the tightening ring is greater than an inner diameter (L2) of the inner sheath.

9. The clip apparatus of claim 1,
wherein the outer sheath is disposed in a space between the handle body and the inner sheath.

10. The clip apparatus of claim 1, further comprising a spring disposed within the moving hole to surround the wire.

11. The clip apparatus of claim 10,
wherein when the spring is uncompressed, the clip coupler is configured to be positioned inside the inner sheath.

12. The clip apparatus of claim 1,
wherein the handle body includes a handle ring disposed at one end of the handle body.

13. The clip apparatus of claim 1,
wherein a sliding movement of the handle slider is limited within a length of the moving hole of the handle body.

* * * * *